(12) United States Patent
Gu et al.

(10) Patent No.: US 10,548,490 B2
(45) Date of Patent: *Feb. 4, 2020

(54) PHYSIOLOGICAL DETECTION DEVICE AND OPERATING METHOD THEREOF

(71) Applicant: PIXART IMAGING INC., Hsin-Chu County (TW)

(72) Inventors: Ren-Hau Gu, Hsin-Chu County (TW); Hsin-Chia Chen, Hsin-Chu County (TW); Raman Sahgal, Santa Clara, CA (US); Jung-Tai Lin, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 850 days.

This patent is subject to a terminal disclaimer.

(21) Appl. No.: 15/231,690

(22) Filed: Aug. 8, 2016

(65) Prior Publication Data

US 2016/0345847 A1 Dec. 1, 2016

Related U.S. Application Data (63) Continuation-in-part of application No. 13/758,304, filed on Feb. 4, 2013, now Pat. No. 9,435,646.

(30) Foreign Application Priority Data

Mar. 1, 2012 (TW) .............................. 101106680 A (51) Int. Cl.
*A61B 5/024* (2006.01)
*A61B 5/11* (2006.01)
(Continued)

(52) U.S. Cl.
CPC ...... *A61B 5/02427* (2013.01); *A61B 5/02438* (2013.01); *A61B 5/1118* (2013.01);
(Continued)

(58) Field of Classification Search
CPC . A61B 5/02427; A61B 5/1118; G06F 3/0383; G06F 1/3259; G06F 3/03543; G01C 11/02
See application file for complete search history.

(56) References Cited

U.S. PATENT DOCUMENTS

2001/0049471 A1* 12/2001 Suzuki ................. A61B 5/0002
600/300
2004/0021637 A1 2/2004 Ahn
(Continued)

FOREIGN PATENT DOCUMENTS

TW 200525437 A 8/2005
TW I244044 B 11/2005

*Primary Examiner* — Shaheda A Abdin
(74) *Attorney, Agent, or Firm* — Hauptman Ham, LLP (57) ABSTRACT

A physiological detection device including a light source, an image sensor and a processor is provided. The light source illuminates a skin surface using a burst mode. The image sensor receives ejected light from skin tissues under the skin surface at a sampling frequency to successively generate image frames. The processor controls the light source and the image sensor, and calculates a physiological characteristic according to the image frames captured when the light source is illuminating light. The physiological detection device reduces the total power consumption by adopting the burst mode.

16 Claims, 9 Drawing Sheets

(51) Int. Cl.
*G01C 11/02* (2006.01)
*G06F 3/0354* (2013.01)

(52) U.S. Cl.
CPC .......... *G01C 11/02* (2013.01); *G06F 3/03543* (2013.01); *G06F 3/03547* (2013.01); *Y02D 10/155* (2018.01)

(56) References Cited

U.S. PATENT DOCUMENTS

2007/0132734 A1 6/2007 Kwak et al.
2007/0222756 A1 9/2007 Wu et al.

* cited by examiner

| | valid frame rate (FPS) | max. detectable speed (IPS) |
|---|---|---|
| high speed | 3000 | 37.8 |
| middle speed | 1500 | 18.9 |
| low speed | 1000 | 12.6 |

| | lighting number of times per second | max. detectable speed (IPS) |
|---|---|---|
| high speed | 1000 | 37.8 |
| middle speed | 1000 | 18.9 |
| low speed | 1000 | 12.6 |

PHYSIOLOGICAL DETECTION DEVICE AND OPERATING METHOD THEREOF

CROSS REFERENCE TO RELATED APPLICATION

This application is a continuation-in-part application of U.S. application Ser. No. 13/758,304, filed on Feb. 4, 2013, and claims the priority benefit of Taiwan Patent Application Serial Number 101106680, filed on Mar. 1, 2012, the full disclosure of which is incorporated herein by reference.

BACKGROUND

1. Field of the Disclosure

This disclosure generally relates to the physiological detection, more particularly, to a physiological detection device and an operating method thereof that employ a burst mode to reduce the power consumption.

2. Description of the Related Art

As a wireless optical mouse does not have a signal line connected to a host, the operational convenience thereof is significantly improved. Especially for an input device of portable computers, the wireless optical mouse gradually replaces the conventional wired optical mouse. However, as the wireless optical mouse generally includes a plurality of active components such as a light source, a digital signal processor, an image sensor and a wireless transmission unit, the total power consumption is large and a service life of the battery is insufficient.

To solve this problem, conventionally it is able to change a sampling frequency and an exposure time of the image sensor so as to reduce the consuming power of a wireless optical mouse. However in practical use, this method can have at least the following problems. As the exposure time of the image sensor is changed with a moving speed of the wireless optical mouse, a total intensity of the image frame being captured can have a large variation resulting in a poor stability.

Figure 1:
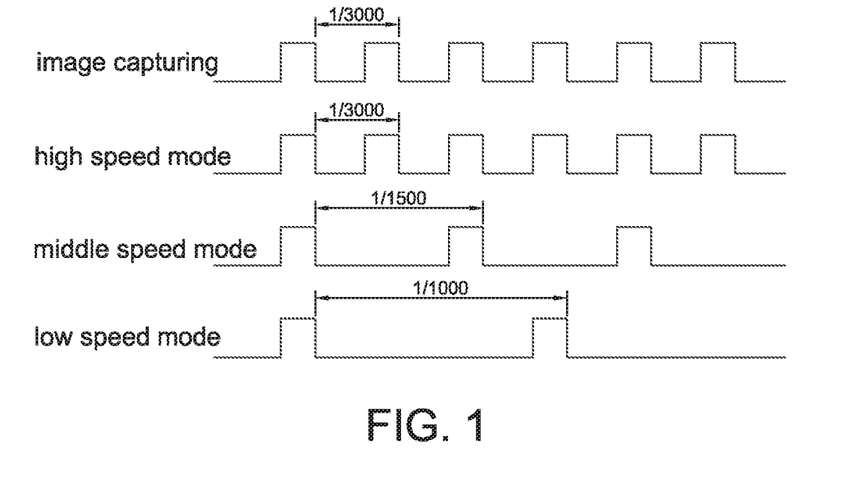
FIG. 1 shows a schematic diagram of the image capturing and the lighting of the light source of the conventional optical mouse.

Another choice to reduce the power consumption of a wireless optical mouse is to change a lighting frequency of the light source. For example referring to FIG. 1, the lighting frequency of the light source may be fixed as 3000 frames/second, 1500 frames/second or 1000 frames/second according to the displacement of the wireless optical mouse. However, in this operating method different consumption current is required at different lighting frequencies, e.g. the consumption current in a high speed mode is triple times of that in a low speed mode.

In addition, the physiological detection device is gradually applied to portable electronic devices and wearable electronic devices. It is an important issue to reduce the power consumption of the physiological detection device.

SUMMARY

It is an object of the present disclosure to provide a physiological detection device and an operating method thereof that adopt the burst light emission to reduce the power consumption.

To achieve the above object, the present disclosure provides a physiological detection device including an image sensor, a light source and a processor. The image sensor is configured to receive, at a sampling frequency, ejected light from skin tissues under a skin surface to generate image frames. The light source is configured to illuminate the skin surface using a burst mode, wherein in the burst mode, the light source is configured to turn on corresponding to N successive image frames and next turn off corresponding to M successive frame intervals. The processor is configured to control the light source and the image sensor, and calculate a physiological characteristic according to the image frames captured when the light source is turned on.

The present disclosure further provides a physiological detection device including an image sensor, a light source and a processor. The image sensor is configured to receive, at a sampling frequency, ejected light from skin tissues under a skin surface to generate image frames. The light source is configured to illuminate the skin surface using a burst mode, wherein in the burst mode, the light source is configured to turn on corresponding to N successive image frames and next turn off corresponding to M successive frame intervals. The processor is configured to control the light source and the image sensor, and calculate a physiological characteristic and an operating state parameter according to the image frames captured when the light source is turned on.

The present disclosure further provides an operating method of a physiological detection device including the steps of: capturing, by an image sensor, ejected light from skin tissues under a skin surface at a sampling frequency to generate image frames; illuminating, by a light source, the skin surface corresponding to N successive image frames, and next turning off the light source corresponding to M successive frame intervals; and calculating, by a processor, a physiological characteristic according to the image frames captured when the light source is illuminating light.

In the embodiment of the present disclosure, the light source turns on corresponding to N successive image frames and next turns off corresponding to M successive image frames, wherein N and M are integers.

In an aspect, the displacement detection device further includes a transmission interface configured to output the displacement and the estimated displacement at a report rate, wherein (M+N) is preferably smaller than or equal to a quotient calculated by dividing a frame rate of the light source by the report rate and N is preferably larger than 4.

In an aspect, the processing unit further calculates an image quality of N image frames and a value of N is increased when the image quality is poor, e.g. lower than a quality threshold.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
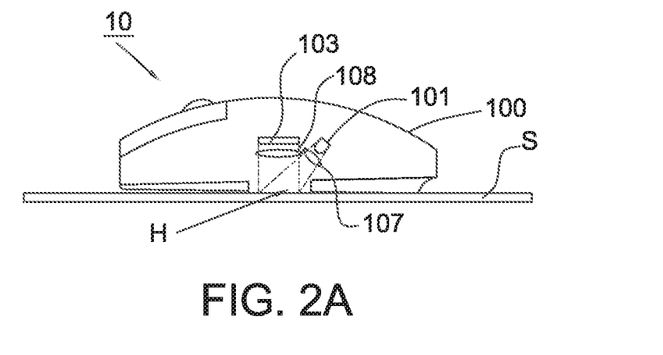
FIG. 2A shows a schematic diagram of the displacement detection device according to an embodiment of the present disclosure.
Figure 2B:
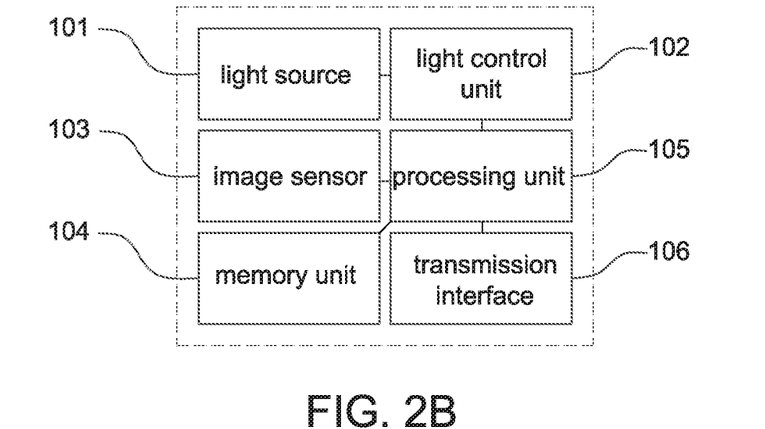
FIG. 2B shows a schematic block diagram of the displacement detection device according to an embodiment of the present disclosure.

Referring to FIGS. 2A and 2B. FIG. 2A shows a schematic diagram of the displacement detection device according to an embodiment of the present disclosure; and FIG. 2B shows a schematic block diagram of the displacement detection device according to an embodiment of the present disclosure, wherein although the displacement detection device 10 is shown as an optical mouse herein, it is not used to limit the present disclosure. For example, the displacement detection device 10 may also be an optical finger mouse (OFM).

The displacement detection device 10 includes a light source 101, a light control unit 102, an image sensor 103, a memory unit 104, a processing unit 105 and a transmission interface 106. In other embodiments, the displacement detection device 10 may further include an optical component 107 configured to adjust an illumination region of the light source 101 and an optical component 108 configured to adjust a sensing efficiency of the image sensor 103.

The image sensor 103 may be a CCD image sensor, a CMOS image sensor or other sensing devices configured to capture image data and the image sensor 103 may capture image frames at a fixed sampling frequency.

The light source 101 may be a light emitting diode or a laser diode and emits infrared light or invisible light in at least one speed mode configured to provide light for the image sensor 103 in capturing the image frames. For example, the light source 101 illuminates a work surface S through an opening H at the bottom surface of a housing 100 of the displacement detection device 10. In addition, when the displacement detection device 10 is an optical finger mouse, the light source 101 is configured to illuminate a finger surface.

The light control unit 102 is configured to control the light source 101 to operate in different speed modes to turn on at at least one lighting frequency or to turn off serially. For example, in a selected speed mode the light source 101 is controlled to illuminate corresponding to (e.g. synchronizing or not synchronizing) a sampling frequency of the image sensor 103. The light source 101 is controlled to turn on corresponding to N successive image frames and next turn off corresponding to M successive image frames alternatively so as to reduce the consuming power of the light source 101 within an interval of the M image frames, wherein a lighting number of times per second of the light source 101 is preferably identical in different speed modes (described later).

The memory unit 104 is coupled to the processing unit 105 and configured to store the displacement (or speed) threshold, the quality threshold and other system parameters.

The processing unit 105 may calculate a displacement or a moving speed according to the correlation between two image frames, compare a current displacement with the displacement threshold (or compare a current moving speed with the speed threshold), and controls the light source 101 through the light control unit 102 according to a comparison result so as to switch between different speed modes, wherein the processing unit 105 may be any processor, such as a digital signal processor (DSP), capable of processing digital image data without any limitation. In the present embodiment, the processing unit 105 calculates a displacement according to the image frames captured when the light source 101 turns on and the displacement may be served as an estimated displacement for an interval during which the light source 101 turns off. For example in one embodiment, the processing unit 105 may calculate a displacement or an average displacement according to the N image frames to be served as an estimated displacement for an interval of the M image frames such that the displacement in the interval of the M image frames is not required to be calculated; that is, the image frames captured in the interval during which the light source 101 turns off may be ignored, The processing unit 105 may switch the speed mode according to the displacement. In addition, the processing unit 105 may further determine a value of N. For example, the processing unit 105 may calculate an image quality of the N image frames and increase the value of N when the image quality is lower than a quality threshold; that is, when the image quality is poor, it is preferably to successively capture more valid image frames to prevent from obtaining an improper estimated displacement, wherein the definition of the image quality is well known and thus details thereof are not described herein. In addition, the processing unit 105 may control the light source 101 through the light control unit 102 to select a larger N in a low speed mode than in a high speed mode.

The transmission interface 106 wired or wirelessly transmits the motion information (e.g. the displacement, average displacement or moving speed) and the estimated motion information (e.g. the estimated displacement, estimated average displacement or estimated moving speed) to an external electronic device, e.g. a computer system or an electronic system having a display unit, at a report rate for corresponding control, Wherein the transmission interface 106 may be a wired or wireless transmission interface and have a report rate of 125 times/second or 120 times/second, but not limited thereto.

Figure 3A:
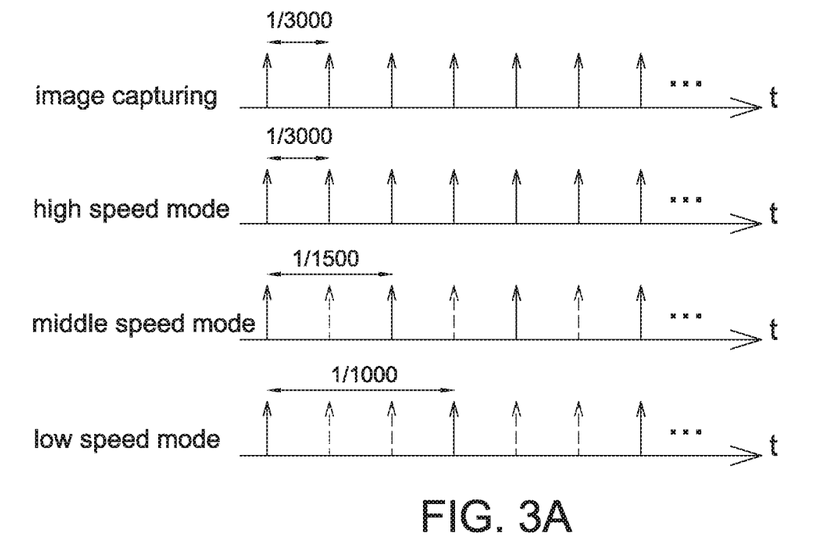
FIG. 3A shows different speed modes of the light source of the displacement detection device according to the embodiment of the present disclosure.

First, different speed modes of the light source 101 in the displacement detection device 10 of the present disclosure are described. Referring to FIG. 3A, it shows a schematic diagram of three speed modes of the light source 101 and the image capturing of the image sensor 103 in the embodiment of the present disclosure, wherein each speed mode corresponds to a lighting frequency. For example in this embodiment, it is assumed that an image sampling period is 1/3000 second, a lighting period of high speed mode is 1/3000 second, a lighting period of middle speed mode is 1/1500 second and a lighting period of low speed mode is 1/1000 second, wherein the lighting periods are multiple times of and synchronized to the image sampling period; that is, the light source 101 provides light for the image sensor 103 in capturing image frames. In this manner, although the image sensor 103 captures the image frames at a fixed sampling frequency, as the light source 101 is controlled by the light control unit 102 not to turn on each time an image frame is captured, a valid image frame captured by the image sensor 13 is determined by the lighting period of the light source 101, wherein the valid image frame referred herein is shown by solid arrows (i.e. light source turning on) in FIG. 3A and dashed arrows indicate the turning off of the light source 101 such that the image sensor 103 is unable to capture the valid image frame (i.e. capturing an invalid image frame). The processing unit 105 calculates the displacement and the moving speed according to the valid image frames captured by the image sensor 103. It is appreciated that values of the image sampling period (or sampling frequency) and the lighting period (or lighting frequency) shown in FIG. 3A are only exemplary and not used to limit the present disclosure.

Figure 3B:
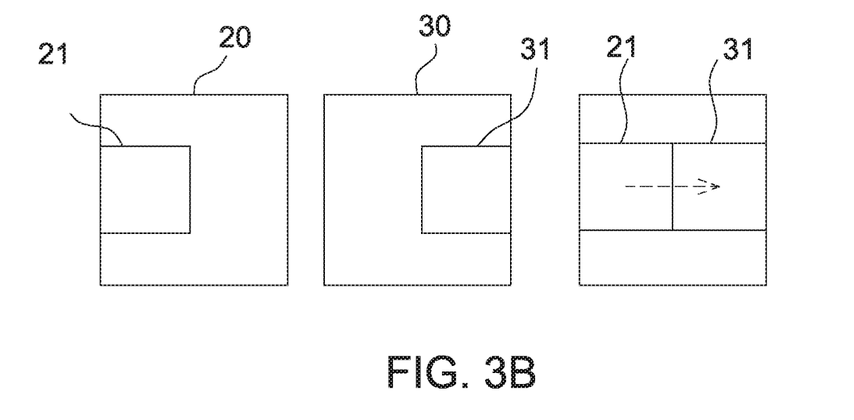
FIG. 3B shows a schematic diagram of calculating a maximum detectable displacement by the displacement detection device according to the embodiment of the present disclosure.

Referring to FIGS. 3A and 3B, next the maximum detectable displacement and the maximum detectable speed between two valid image frames that can be detected by the processing unit 105 are described. In one embodiment, the image sensor 103 captures two valid image frames, e.g. a first image frame 20 and a second image frame 30, corresponding to the turning on of the light source 101. The processing unit 105 selects a reference search block 21 in the first image frame 20 and selects a search block 31 in the second image frame 30. The processing unit 105 then calculates a distance between the reference search block 21 and the search block 31 to be served as a current displacement detected by the displacement detection device 10. For simplification, only displacement in X-axis (e.g. the horizontal direction in the figure) is considered in FIG. 3B and both X-axis component and Y-axis component may be included in actual operation. The maximum detectable displacement may be obtained when the reference search block 21 locates at the most left side of the first image frame 20 and the search block 31 locates at the most right side of the second image frame 30. In this embodiment, it is assumed that every image frame has 16×16 pixels (i.e. the size of a sensing array of the image sensor), and the search block 31 and the reference search block 21 have 8×8 pixels, and thus the maximum detectable displacement between two valid image frames that the processing unit 105 may detect is 8-pixels distance (i.e. maximum detectable pixel numbers). As the maximum detectable displacement is determined according to the size of every image frame, it is not affected by the lighting frequency of the light source 101; that is, the maximum detectable displacement is always the same in every speed mode of the light source 101.

Accordingly, when a displacement of the displacement detection device 10 between two successive valid image frames exceeds 8-pixels distance, the light source 101 has to shorten the lighting period such that the processing unit 105 is able to detect the displacement. In other words, when a displacement of the displacement detection device 10 exceeds the maximum detectable displacement, the processing unit 105 is unable to calculate the displacement such that the lighting period of the light source 101 has to be shortened so that the displacement detection device 10 can operate normally. Therefore, the processing unit 105 may control the light source 101 to enter different speed modes, e.g. a high speed mode, a middle speed mode or a low speed mode, according to the displacement calculated thereby, such as the displacement mentioned above. It is appreciated that each value referred in this embodiment is only an exemplary and not used to limit the present disclosure.

Figure 3C:
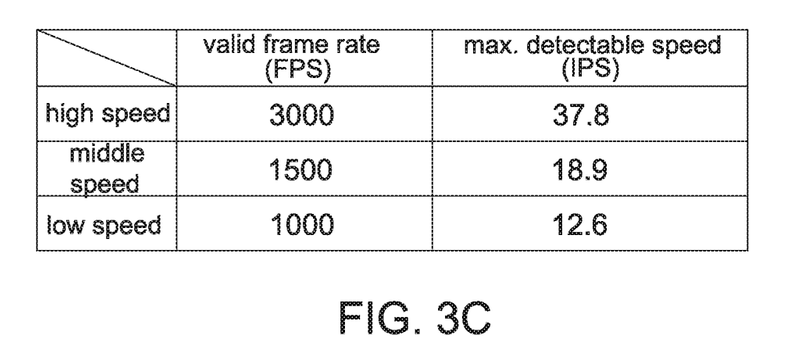
FIG. 3C shows the valid frame rate and the corresponding maximum detectable speed in the displacement detection device according to the embodiment of the present disclosure.

However, the maximum detectable speed in different speed modes may be different. For example, it is assumed that each pixel has a pixel size 40×40 micrometer and thus a maximum detectable speed in each speed mode may be calculated as the maximum detectable pixel numbers×pixel size×frame rate. Therefore, the maximum detectable speed in the high speed mode equals 8×40×3000=37.8 inches/second (IPS). Similarly, maximum detectable speeds of the middle speed mode and the low speed mode are shown in FIG. 3C, wherein the valid frame rate is a reciprocal of the lighting period of the light source 101.

In order to further reduce the power consumption of the light source 101 of the displacement detection device 10, in the present disclosure a lighting number of times per second of the light source 101 in the high speed mode and middle speed mode is designed to be identical to that in the low speed mode. Therefore, the light source 101 may emit light in the lowest lighting number of times per second so as to effectively reduce the power consumption thereof.

Figure 4A:
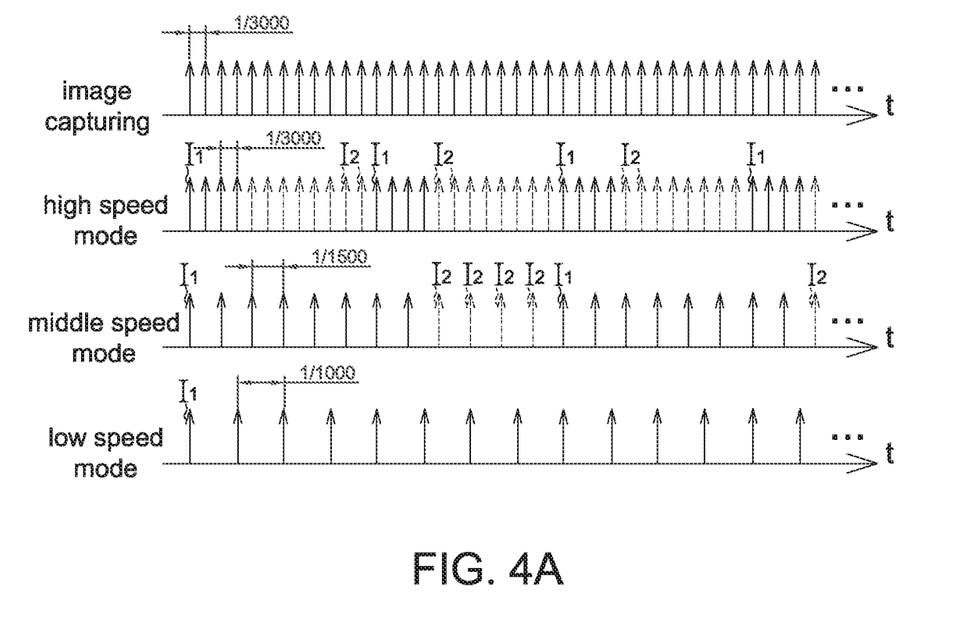
FIG. 4A shows a schematic diagram of the image capturing and the lighting of the light source of the displacement detection device according to the embodiment of the present disclosure.

Referring to FIG. 4A, it shows a schematic diagram of the image capturing and the lighting of the light source of the displacement detection device 10 according to the embodiment of the present disclosure. The speed mode of the light source 101 is determined at first. The image sensor 103 captures image frames at a fixed sampling frequency (e.g. 3000 frames/second) and the light source 101 successively illuminates synchronizing to the sampling frequency. The processing unit 105 calculates a displacement according to the image frames captured by the image sensor 103 and determines a speed mode, e.g. a high speed mode, a middle speed mode or a low speed mode, according to a comparison result of comparing the displacement with at least one displacement threshold. Next, the processing unit 105 notifies the light control unit 102 to control the light source 101 with the selected speed mode to illuminate in different lighting patterns; for example, turning on corresponding to N successive image frames to allow the image sensor 103 to capture N valid image frames within an interval of the N image frames and next turning off corresponding to M successive image frames such that the image sensor 103 is not able to capture the valid image frame within an interval of the M image frames. For example in FIG. 4A, $I_1$ indicates valid image frames corresponding to the N image frames and $I_2$ indicates invalid image frames corresponding to the M image frames. For example in FIG. 4A, in the high speed mode the light source 101 turns on corresponding to 4 successive image frames and then turns off corresponding to 8 successive image frames; in the middle speed mode the light source 101 turns on corresponding to 8 successive image frames and then turns off corresponding to 4 successive image frames; and in the low speed mode the light source 101 turns on at the fixed lighting frequency. It is appreciated that in FIG. 4A numbers of the turning on (i.e. N) and the turning off (i.e. M) of the light source 101 are only exemplary embodiments but not limitations to the present disclosure.

The processing unit 105 then calculates a displacement according to the valid image frames, e.g. calculating a displacement or an average displacement according to the N image frames to be served as an estimated displacement for an interval of the M image frames. Preferably, a value of N is larger than or equal to 4 so that the processing unit 105 is able to correctly estimate the estimated displacement for the interval of the M image frames. In one embodiment, a value of N in the low speed mode is larger than a value of N in the high speed mode so as to increase the system stability. In addition, as the interval of the M image frames is limited by the report rate of the transmission interface 106, the interval of the M image frames is preferably shorter than 8 milliseconds (in the case of 125 times/second report rate), or (M+N) is preferably lower than a quotient calculated by dividing a frame rate of the light source 101 (herein the frame rate refers to a reciprocal of a time interval between two successive lighting of the light source 101 in a speed mode) by the report rate so as to avoid error in calculating the displacement. For example when the report rate is 125 times/second, (M+N) is preferably lower than 25 in the high speed mode and (M+N) is preferably lower than 13 in the middle speed mode, wherein values referred herein are only exemplary.

Figure 4B:
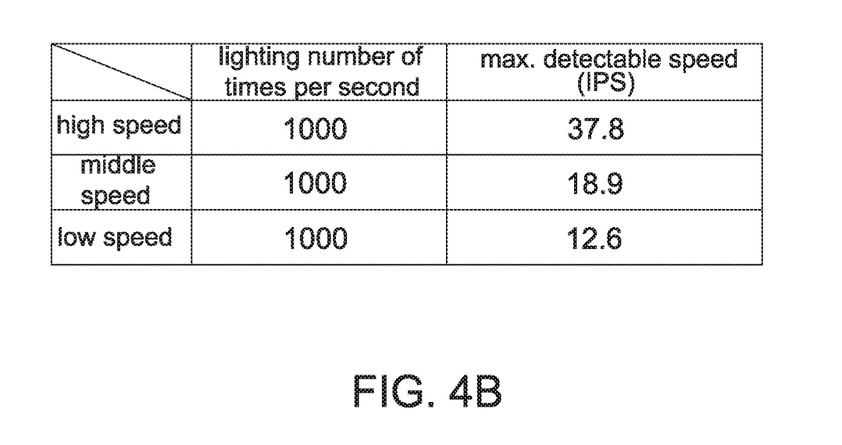
FIG. 4B shows the lighting number of times per second of the light source and the corresponding maximum detectable speed in the displacement detection device according to the embodiment of the present disclosure.

Referring to FIG. 4B, through the aforementioned operating method, the light source 101 turns on 1000 times per second and the current consumption of the light source 101 in every speed mode is identical and the total power consumption herein is lower than that in FIG. 3A. In addition, as the image sensor 103 captures the image frames at its original sampling frequency within the interval of the N image frames, the maximum detectable speed here is still maintained identical to that shown in FIG. 3C.

The operating method of the displacement detection device according to the embodiment of the present disclosure includes the steps of: capturing, with an image sensor, image frames at a sampling frequency; controlling a light source to turn on at at least one lighting frequency or to turn off serially; and calculating, with a processing unit, a displacement according to the image frames captured when the light source turns on to be served as an estimated displacement for an interval during which the light source turns off.

Figure 5A:
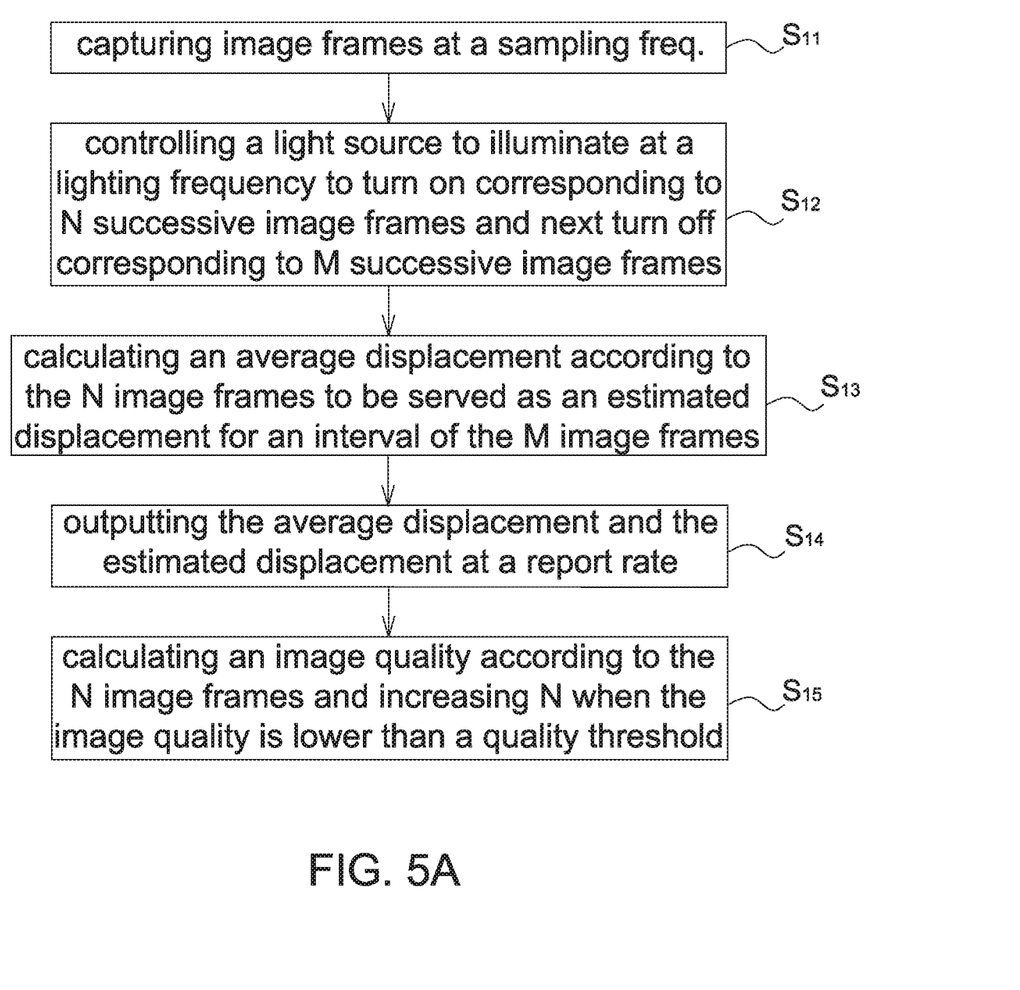
FIGS. 5A to 5B show the flow chart of the operating method of the displacement detection device according to the embodiment of the present disclosure.

Referring to FIGS. 4A and 5A, for example in one aspect the operating method of the displacement detection method of the present disclosure includes the steps of: using the image sensor 103 to capture image frames at a fixed sampling frequency (Step $S_{11}$); controlling the light source 101 to turn on at a lighting frequency corresponding to N successive image frames such that the image sensor 103 may successively capture N valid image frames and next to turn off corresponding to M successive image frames so as to reduce the consuming power of the light source 101 in an interval of the M image frames (Step $S_{12}$); and using the processing unit 105 to calculate a displacement according to the N valid image frames to be served as an estimated displacement for the interval of the M image frames (Step $S_{13}$). In this embodiment, a value of N is preferably larger than 4. The operating method may further include the steps of: outputting, using the transmission interface 106, the displacement and the estimated displacement at a report rate, wherein (M+N) is smaller than or equal to a quotient calculated by dividing a frame rate of the light source 101 by the report rate so as to prevent obtaining improper displacement (Step $S_{14}$); and calculating, using the processing unit 105, an image quality according to the N image frames and increasing a value of N when the image quality is lower than a quality threshold thereby increasing the calculation accuracy (Step $S_{15}$).

The operating method of the displacement detection method according to another embodiment of the present disclosure includes the steps of: capturing, with an image sensor, image frames at a sampling frequency; turning on a light source synchronizing to the sampling frequency; calculating, with a processing unit, a displacement according to the image frames captured by the image sensor to accordingly determine a speed mode of the light source; controlling the light source to turn on in the speed mode or to turn off serially; and calculating, with the processing unit, a displacement according to the image frames captured when the light source turns on to be served as an estimated displacement for an interval during which the light source turns off.

Figure 5B:
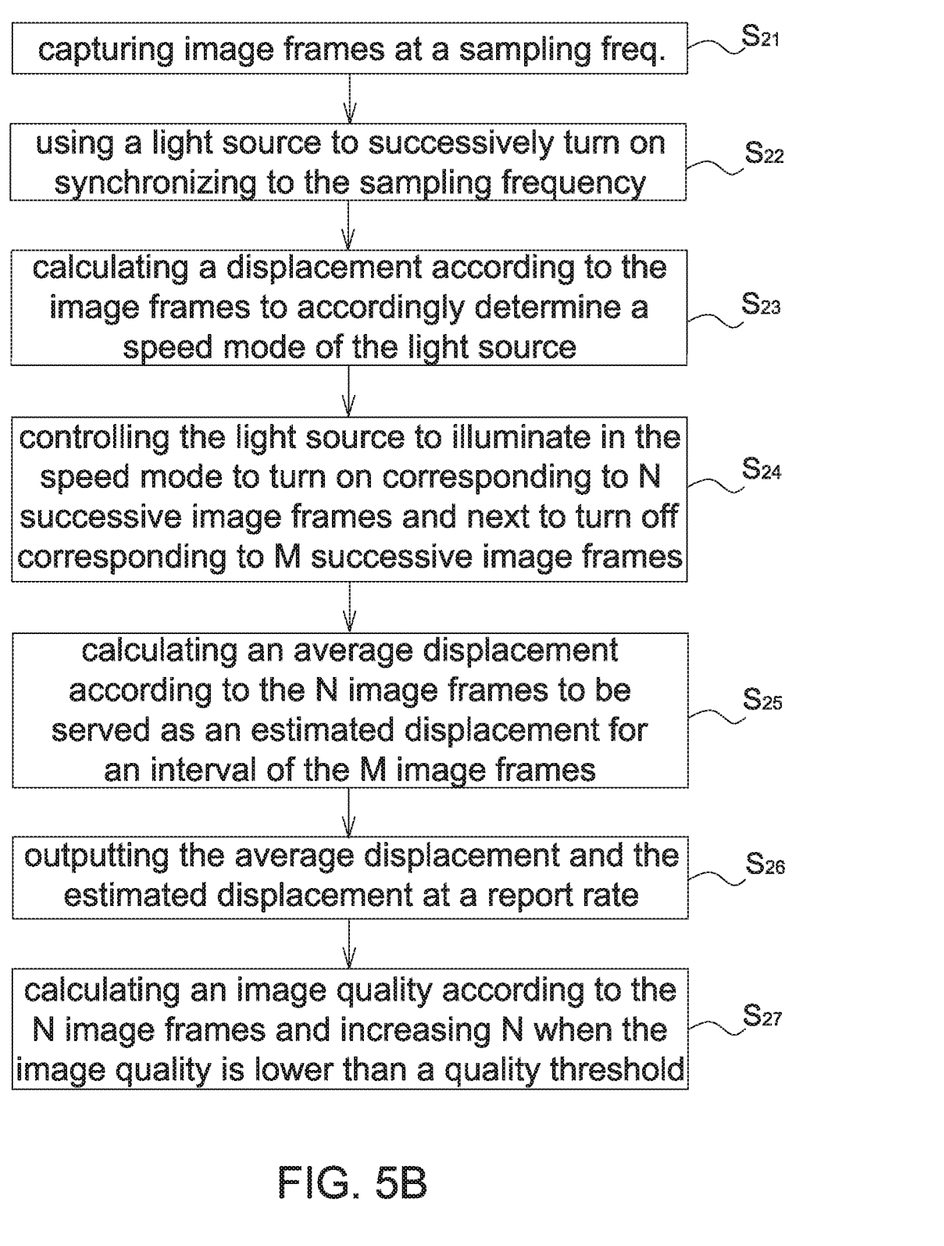

Referring to FIGS. 4A and 5B, for example in one aspect the light source 101 of the displacement detection device 10 has a plurality of speed modes and the operating method of the displacement detection device of the present disclosure includes the steps of: using the image sensor 103 to capture image frames at a fixed sampling frequency (Step $S_{21}$); using the light source 101 to successively turn on synchronizing to the sampling frequency (Step $S_{22}$); using the processing unit 105 to calculate a displacement according to the image frames captured by the image sensor 103 to accordingly determine a speed mode of the light source (Step $S_{23}$); controlling the light source 101 to illuminate in the speed mode to turn on corresponding to N successive image frames such that the image sensor 103 may successively capture N valid image frames and next to turn off corresponding to M successive image frames so as to reduce the power consumption of the light source 101 in an interval of the M image frames (Step $S_{24}$); and using the processing unit 105 to calculate a displacement according to the N valid image frames to be served as an estimated displacement for an interval of the M image frames (Step $S_{25}$). In this embodiment, the processing unit 105 may further real-timely switch the speed mode according to the displacement. In this embodiment, a value of N in the low speed mode is preferably larger than a value of N in the high speed mode so as to increase the system stability. Similarly, a value of N is preferably larger than 4 so as to increase the calculation accuracy of the displacement. This embodiment may further include the steps of: outputting, with the transmission interface 106, the displacement and the estimated displacement at a report rate, wherein (M+N) is smaller than or equal to a quotient calculated by dividing a frame rate of the light source 101 by the report rate so as to avoid obtaining improper displacement (Step $S_{26}$); and calculating, with the processing unit 105, an image quality according to the N image frames and increasing a value of N when the image quality is lower than a quality threshold so as to increase the calculation accuracy (Step $S_{27}$), It should be mentioned that the light source 101 in Step $S_{22}$ may successively turn on in any speed mode, e.g. turning on corresponding to successive 2 to 3 image frames or more than 3 image frames. In this embodiment, said valid image frames refer to the image frames captured when the light source 101 is turned on.

In the embodiments of the present disclosure, the light source 101 turns on corresponding to N successive image frames and next turns off corresponding to M successive image frames. The processing unit 105 calculates a displacement according to the image frames captured when the light source 101 turns on to be served as a reference displacement, and the reference displacement may be served as a displacement for an interval during which the light source 101 turns off.

The burst mode used in the above displacement detection device is also applicable to an optical physiological detection device so as to reduce the total power consumption of an analog circuit. Generally, the optical physiological detection device will capture a preoperative image before capturing a valid image frame to allow analog switches to reach a stable state and for auto exposure (AE) convergence. Although the preoperative image is not used to calculate the physiological characteristic, it can increase the total power consumption. The present disclosure employs a burst mode to successively capture valid image frames within a short interval (i.e. the burst period) and not to capture image frames within a longer interval so as to reduce a number of preoperative images being generated (i.e. one preoperative image being generated only before each burst period). Accordingly, the power consumption of the analog circuit is effectively reduced.

Figure 6:
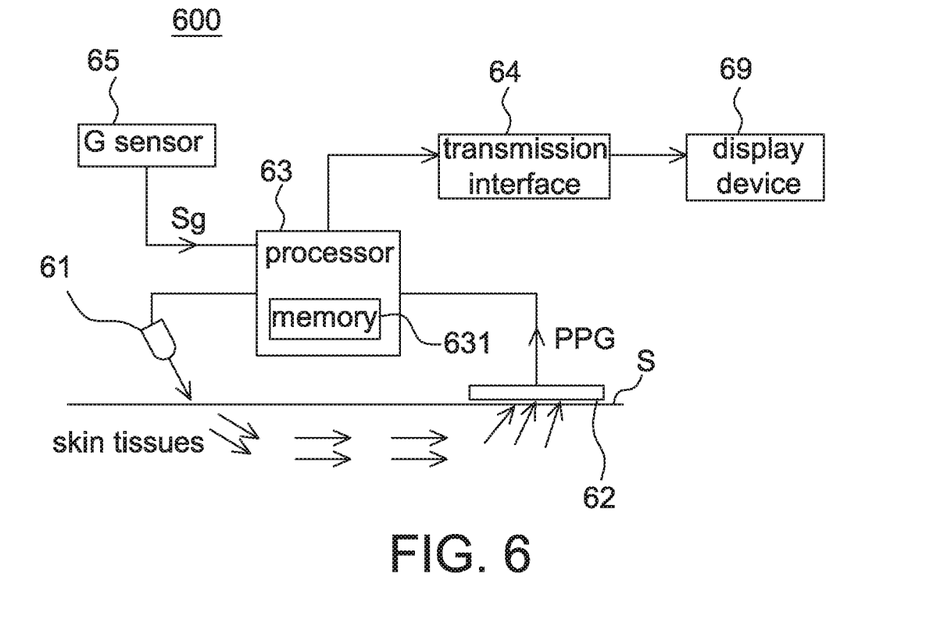
FIG. 6 is a schematic block diagram of a physiological detection device according to one embodiment of the present disclosure.

Please referring to FIG. 6, it is a schematic block diagram of a physiological detection device 600 according to one embodiment of the present disclosure. The physiological detection device 600 includes a light source 61, an image sensor 62, a processor 63 and a transmission interface 64. In some embodiments, the physiological detection device 600 further includes a display device 69 configured to display a detection result of the physiological detection device 600, e.g., the pulse rate, respiration rate, blood pressure, blood oxygenation and so on. In some embodiments, the transmission interface 64 of the physiological detection device 600 is coupled to an external display device 69 in a wired or wireless manner to output the detection result of the physiological detection device 600 to the external display device 69 to be real-timely displayed thereon. In other words, the display device 69 may or may not be included in the physiological detection device 600 depending on different applications. The wired and wireless communication techniques are known to the art, and thus details thereof are not repeated herein.

The display device 69 is, for example, a liquid-crystal display (LCD), a plasma display panel (PDP), an organic light-emitting diode (OLED) display or a projector for displaying images without particular limitations as long as it is able to display the above physiological characteristic by graphs, characters or numbers on a screen. In other embodiments, the display device 69 includes, for example, a speaker for prompting the above physiological characteristic by sounds.

The light source 61 is, for example, a light emitting diode or a laser diode, and configured to emit light adapted to penetrate and be absorbed by skin tissues. For example, a wavelength of light emitted by the light source 61 is about 610 nm or 910 nm, but not limited thereto. The light source 61 illuminates a skin surface S to allow light to pass through skin tissues under the skin surface S. Preferably, the physiological detection device 600 includes a transparent surface to be attached to the skin surface S in operation and for protecting the light source 61, and the light source 61 is arranged at an inner side of the transparent surface. The transparent surface is made of transparent materials, e.g., plastic or glass, without particular limitations. In some embodiments, the transparent surface is a surface of a light guide which has the function of guiding light paths.

Figure 9:
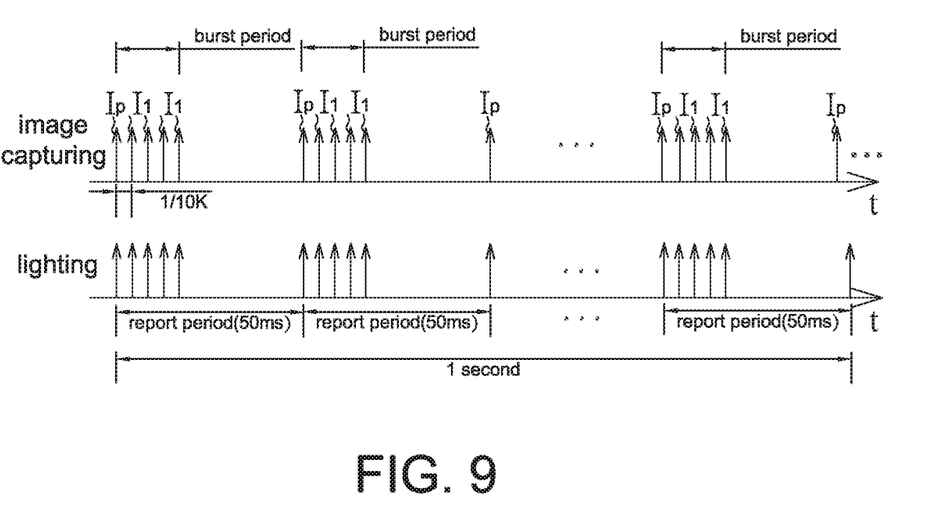
FIG. 9 is an operational schematic diagram of a physiological detection device according to one embodiment of the present disclosure.

In the present disclosure, the light source 61 illuminates the skin surface S using a burst mode. In the burst mode, the light source 61 is turned on corresponding to N successive image frames, and next turned off corresponding to M successive frame intervals, wherein N and M are integers. In FIG. 9, the light source 61 is shown to be turned on corresponding to 5 images within a burst period, wherein N=5 is only intended to illustrate but not to limit the present disclosure. As shown in FIG. 9. the N successive image frames are at initial phase of a report period, and the M successive frame intervals are at a residual phase of the report period.

In some embodiments, when the physiological detection device 600 is also used to detect the blood oxygenation, the physiological detection device 600 includes two light sources to respectively emit light of different wavelengths, wherein a method of detecting the blood oxygenation may be referred to U.S. application Ser. No. 13/614,999 assigned to the same assignee of the present application, and the full disclosure of which is incorporated herein by reference.

Figure 7:
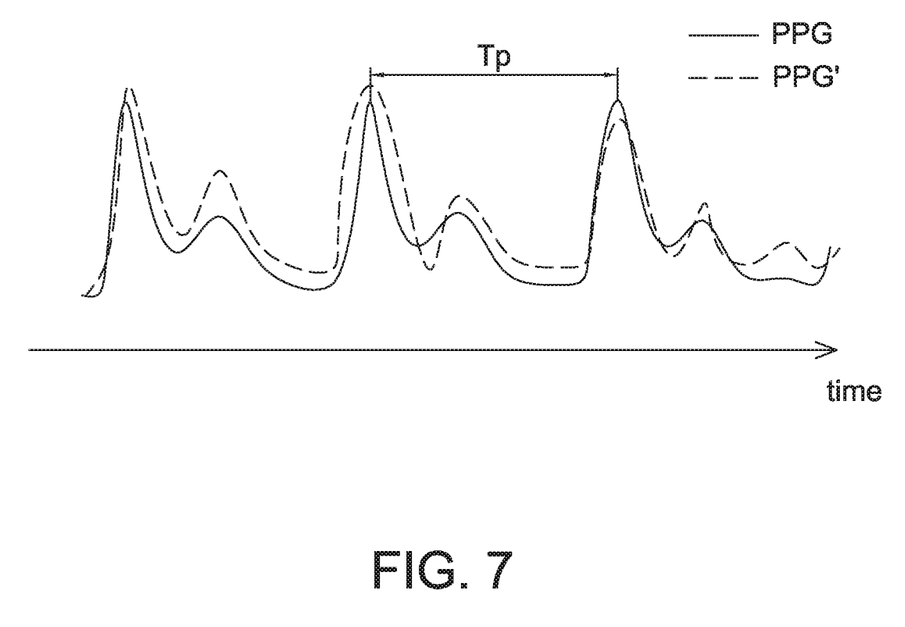
FIG. 7 is a schematic diagram of a photoplethysmography (PPG) signal detected by a physiological detection device according to one embodiment of the present disclosure.

The image sensor 62 includes an image sensor array, e.g., a CMOS sensor array, which has a pixel number. The image sensor 62 is configured to detect ejected light emitted from the skin tissues under a skin surface S to successively generate image frames within a burst period, e.g., outputting valid image frames $I_1$ when the light source 21 is being turned on (referring to FIG. 9), wherein the sampling frequency is preferably much larger than the heartbeat to facilitate the operation of burst mode. A first image frame Ip captured within each burst period is a preoperative image which is generally used for the auto exposure convergence and other circuit adjusting requirements but is not for calculating heart rates. The image sensor 62 further generates a PPG signal according to the valid image frames $I_1$, as shown in FIG. 7 for example. In FIG. 7, PPG and PPG' represent photoplethysmography signals of a same user acquired within different time intervals. In one embodiment, each pixel of the image sensor array respectively outputs the PPG signal mentioned herein. In other embodiments, an intensity sum of all pixels or a part of pixels of the image sensor array is used as the PPG signal mentioned herein. Similarly, the image sensor 62 is arranged inside the transparent surface.

A method of detecting a three dimensional physiology distribution by an image sensor array may be referred to U.S. application Ser. No. 14/955,463 assigned to the same assignee of the present application, and the full disclosure of which is incorporated herein by reference.

In some embodiments, the image sensor 62 is replaced by a single photodiode to output a PPG signal according to detection results at different time intervals.

Figure 8A:
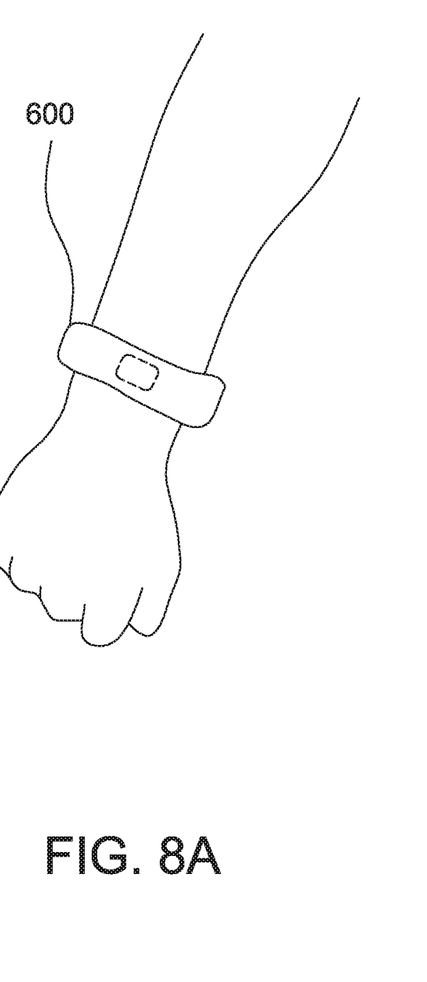
FIGS. 8A and 8B are usage states of a physiological detection device according to some embodiments of the present disclosure.
Figure 8B:
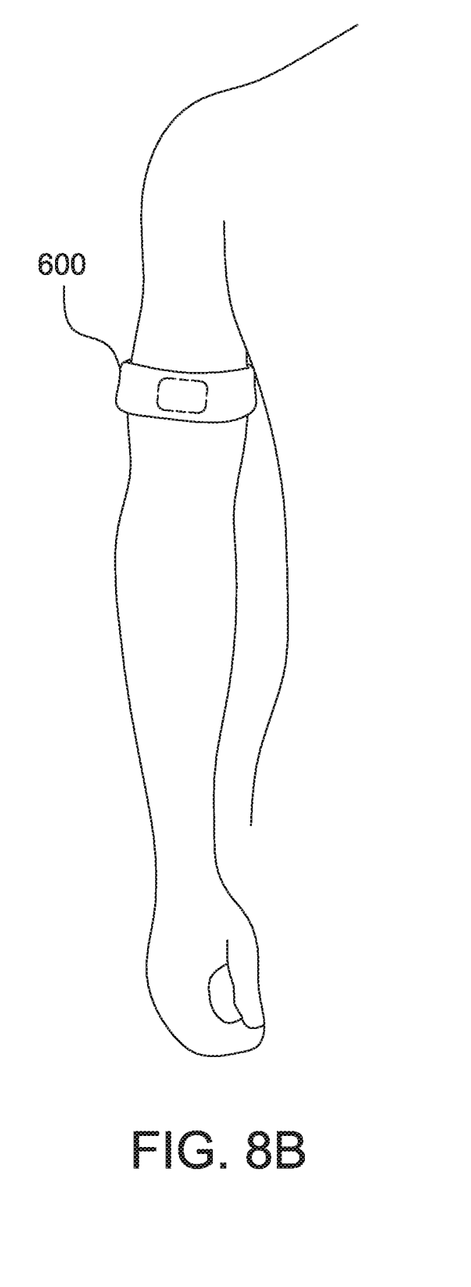

Please referring to FIGS. 8A and 8B, they are usage states of a physiological detection device according to some embodiments of the present disclosure. The physiological detection device 600 analyzes and displays the variation of a user's physiological characteristic changed with time by detecting a PPG signal of the user's skin tissues. Accordingly, the physiological detection device 600 is able to be arranged at any suitable location for detecting the PPG signal, e.g., setting on the user's wrist (FIG. 8A) or the user's arm (FIG. 8B), but not limited thereto, in other embodiments, the physiological detection device 600 is integrated in a portable electronic device or a wearable electronic device, e.g., a bracelet, an armband, a ring, a foot ring, a foot bracelet, a cell phone, an earphone, a headphone and a personal digital assistant (PDA) which contacts at least a part of skin surface of a user. In addition, the physiological detection device 600 is able to be coupled to a medical device, a home appliance, a vehicle, a security system in a wired or wireless way. Preferably, the one connected with the physiological detection device 600 includes a display device to real-timely display a detection result of the physiological detection device 600.

The processor 63 is, for example, a digital signal processor (DSP), a microcontroller (MCU), a central processing unit (CPU) or an application specific integrated circuit (ASIC), which is electrically coupled to the light source 61 and the image sensor 62, and is configured to control the light source 61 and the image sensor 62 to operate correspondingly (referring to FIG. 9).

In one embodiment, the processor 63 calculates a physiological characteristic and an image quality according to the image frames captured when the light source 61 is turned on (i.e. valid image frames $I_1$), and adjusts values of N and M according to the calculated image quality, wherein the physiological characteristic includes the pulse rate, respiration rate, blood pressure, blood oxygenation and so on. It is possible to use conventional methods to calculate the above physiological characteristics according to the PPG signal. The present disclosure is to use a burst mode to capture the image frames which are used to generate the PPG signal.

Referring to FIG. 9, it is an operational schematic diagram of a physiological detection device according to one embodiment of the present disclosure. The image sensor 62 generates image frames at a fixed sampling frequency (e.g., 10 KHZ shown herein). In this embodiment, the light source 61 is successively turned on for 5 times (i.e. N=5) synchronizing to the sampling frequency, and then turned off continuously to the end of a report period. As mentioned above, in addition to the preoperative image, the image frames captured when the light source 61 is being turned on is referred to valid image frames $I_1$.

The transmission interface 64 outputs the physiological characteristic at a report rate (e.g., 20 HZ, but not limited to). That is, the transmission interface 64 outputs the physiological characteristic every a report period (e.g., 500 ms shown herein, but not limited to). In one embodiment, the N successive image frames (e.g., first 5 image frames) correspond to an initial interval of the report period, and N is larger than or equal to 5 to correctly calculate the physiological characteristic.

In one embodiment, when all pixels are sequentially read by a same read circuit, (N+M) is a quotient calculated by dividing the sampling frequency by a product of the report rate and the pixel number, i.e. (N+M)=(sampling frequency)/(report rate)×(pixel number)). When the image sensor 62 is a single photodiode, the pixel number is 1. In the embodiment of FIG. 9, (N+M)=10K/(20×1)=500. That is, the image sensor 62 acquires 5 image signals within each report period, wherein the first signal is a preoperative image signal, the second to fourth signals are valid image signals and the following 495 signals are not acquired. The processor 63 then calculates the physiological characteristic, image quality and operating state parameter according to valid N image signals of every report period. When the image sensor 62 is a sensor array having 2×2 pixels, the pixel number is 4. In the embodiment of FIG. 9, (N+M)=10K/(20×4)=125. That is, the image sensor 62 acquires 5 image frames within each report period, wherein the first frame is a preoperative image frame, the second to fourth frames are valid image frames and the following 120 frames are not acquired. The processor 63 then calculates the physiological characteristic, image quality and operating state parameter according to valid N image frames of every report period. In another embodiment, when all pixels are read simultaneously, (N+M) is a quotient calculated by dividing the sampling frequency by the report rate, i.e. (N+M)=(sampling frequency)/(report rate).

It should be mentioned that the pixel number herein is referred to an effective pixel number which is equal to a number of PPG signals being outputted in each frame. For example, when the sensor array includes 4×4 pixels, it is possible that the sensor array calculates, by circuit arrangement, a gray value sum of 4 pixel groups each having 2×2 pixels to be respectively used as a PPG signal, i.e. 4 PPG signals being outputted in each frame. Accordingly, the pixel number of this embodiment is 4 instead of 16.

Figure 10:
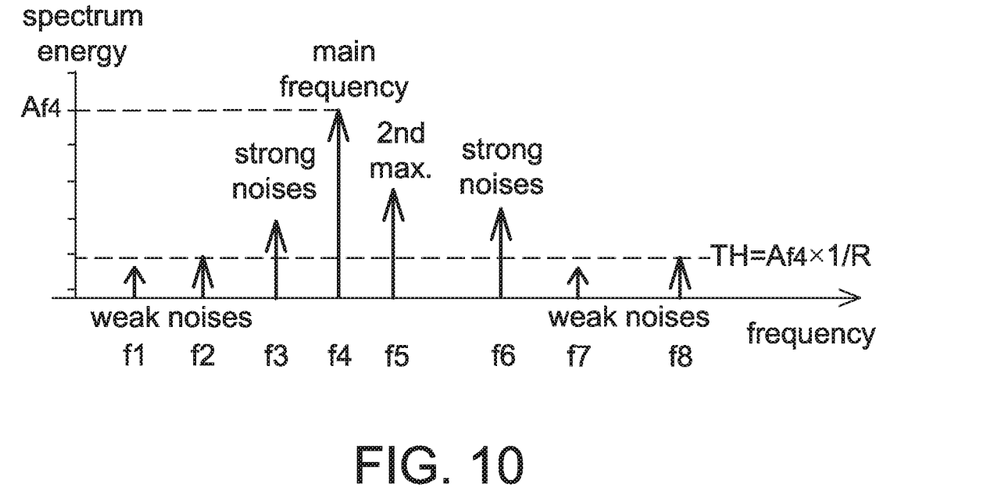
FIG. 10 is a schematic diagram of frequency data converted from a PPG signal by a physiological detection device according to one embodiment of the present disclosure.

In one embodiment, the processor 63 is configured to calculate a first heartbeat at a time domain and a second heartbeat at a frequency domain according to the image frames captured when the light source 61 is turned on (i.e. the valid image frames $I_1$), and use a difference value between the first heartbeat and the second heartbeat to indicate the image quality. For example, the processor 63 obtains the PPG signal as shown in FIG. 7 according to the valid image frames $I_1$. The processor 63 calculates a reciprocal of a time interval between two peaks (e.g., 1/Tp) directly in the time domain to be used as a first heartbeat. The processor 63 further converts the PPG signal to the frequency domain, e.g., using the fast Fourier transform (FFT), but not limited to, to generate frequency data as shown in FIG. 10. The processor 63 takes, for example, a main frequency (e.g., f4) as a second heartbeat. When a difference value between the first heartbeat and the second heartbeat is within a predetermined range, it means that the image quality is good and thus the processor 63 selects a lower N among pre-stored N values. On the contrary, when the difference value between the first heartbeat and the second heartbeat exceeds the predetermined range, it means that the main frequency f4 may be caused by motion noises and thus the processor 63 selects a higher N among the pre-stored N values to improve the reliability of the image capturing.

In another embodiment, the processor 63 is configured to obtain a main frequency spectrum energy $A_{f4}$ of a main frequency f4 at a frequency domain according to the image frames captured when the light source 61 is turned on (i.e. the valid image frames $I_1$) as shown in FIG. 10. The processor 63 multiplies the main frequency spectrum energy $A_{f4}$ by a predetermined ratio smaller than 1 (e.g., 1/R and R is larger than 1) to obtain an energy threshold TH, and uses a number of frequencies whose spectrum energy is larger than the energy threshold TH to indicate the image quality, wherein the predetermined ratio 1/R is determined according to the sensitivity and noise tolerance of the device. For example in FIG. 10, the predetermined ratio is selected as 1/4, and the number of frequencies whose spectrum energy larger than the energy threshold TH is 3 (e.g., f3, f5 and f6). In the frequency data of FIG. 10, when the number of frequencies is higher, it means that the valid image frames $I_1$ include more noises and the image quality is lower; on the contrary, the image quality is better. The processor 63 is arranged to select a higher N among pre-stored N values or increase the value of N when the number of frequencies is larger than or equal to a predetermined number (e.g., 2) to improve the reliability of the image capturing; on the contrary, the processor 63 selects a lower N among the pre-stored N values or decreases the value of N, wherein the predetermined number is determined according to different applications.

In another embodiment, the processor 63 is configured to obtain a main frequency spectrum energy $A_{f4}$ of a main frequency f4 at a frequency domain according to the image frames captured when the light source 61 is turned on (i.e. the valid image frames $I_1$) as shown in FIG. 10. The processor 63 multiplies the main frequency spectrum energy $A_{f4}$ by a predetermined ratio smaller than 1 (e.g., 1/R and R is larger than 1) to obtain an energy threshold TH, and uses a sum of spectrum energy of those frequencies whose spectrum energy is larger than the energy threshold TH (e.g., energy sum of the main frequency, second maximum frequency and strong noises, or energy sum of the second maximum frequency and strong noises in FIG. 10) to indicate the image quality, wherein the predetermined ratio 1/R is determined according to the sensitivity and noise tolerance of the device. In the frequency data of FIG. 10, when the sum of spectrum energy is higher, it means that the valid image frames $I_1$ contain more noises and the image quality is lower; on the contrary, the image quality is better. The processor 63 is arranged to select a higher N among pre-stored N values or increase the value of N when the sum of spectrum energy is larger than or equal to a predetermined energy sum to improve the reliability of the image capturing; on the contrary, the processor 63 selects a lower N among the pre-stored N values or decreases the value of N. It should be mentioned that the naming of noises in FIG. 10 is only intended to illustrate but not to limit the present disclosure.

In another embodiment, the processor 63 calculates a physiological characteristic and an operating state parameter according to the image frames captured when the light source 61 is turned on (i.e. the valid image frames $I_1$), and adjusts values of N and M according to the operating state parameter. In this embodiment, the processor 63 calculates the operating state parameter according to the PPG signal or the output of a G sensor.

For example, the processor 63 is configured to generate a photoplethysmography (PPG) signal according to the image frames captured when the light source 61 is turned on (i.e. the valid image frames $I_1$), and use a waveform variation of the PPG signal to indicate the operating state parameter. Generally, when a same user is in a rest state, the PPG signal has a specific shape. And shapes between different users have some differences. According to this feature, a variation of the specific shape (e.g., by calculating the correlation or similarity between specific shapes of PPG and PPG' acquired at different time intervals) is used as the operating state parameter. When the variation of the specific shape exceeds a predetermined variation (e.g., the correlation or similarity between PPG and PPG' being smaller than a predetermined value), it means that a user enters a sports state; whereas, when the variation of the specific shape does not exceed the predetermined variation (e.g., the correlation or similarity between PPG and PPG' being larger than the predetermined value), it means that the user is still in a rest state.

For example, the physiological detection device 600 further includes a G sensor 65 configured to output an acceleration signal Sg. The type of the G sensor 65 does not have particular limitations as long as it is able to generate the acceleration signal Sg when a user has motions. Since the acceleration signal Sg of the G sensor 65 reflects the activity of the user, in the present disclosure the acceleration signal Sg (e.g., at least one of accelerations in three dimensions) is used as the operating state parameter. When the acceleration signal Sg exceeds a predetermined acceleration, it means that a user enters a sports state; whereas, when the acceleration signal Sg does not exceed the predetermined acceleration, it means that the user is still in a rest state. The predetermined acceleration is set and stored respectively associated with different users and according to the sensitivity and noise tolerance of the device.

It should be mentioned that the rest state in the present disclosure is not referred that a user is completely motionless but referred to the motion of the user is not large enough to make the physiological detection device 600 be unable to accurately detect the physiological characteristic. When the operating state parameter indicates a sports state, the processor 63 uses a larger N among pre-stored N values or increases the value of N. When the operating state parameter indicates a rest state, the processor 63 uses a smaller N among pre-stored N values or decreases the value of N.

In other embodiments, the G sensor 65 is also applicable to the above embodiment which adjusts values of N and M according to the image quality. For example, the processor 63 converts the acceleration signal Sg to the frequency domain at first and obtains at least one sports frequency, and then removes the frequency in the frequency data of FIG. 10 related to the sports frequency thereby removing noises (i.e. the frequency related to the sports frequency is treated as noises). The processor 63 then calculates the image quality (e.g., calculating a number of frequencies or energy sum of frequencies whose spectrum energy is larger than the energy threshold TH) according to the denoised frequency data (i.e. the sports frequencies being removed) to confirm whether N should be adjusted or not.

Figure 11:
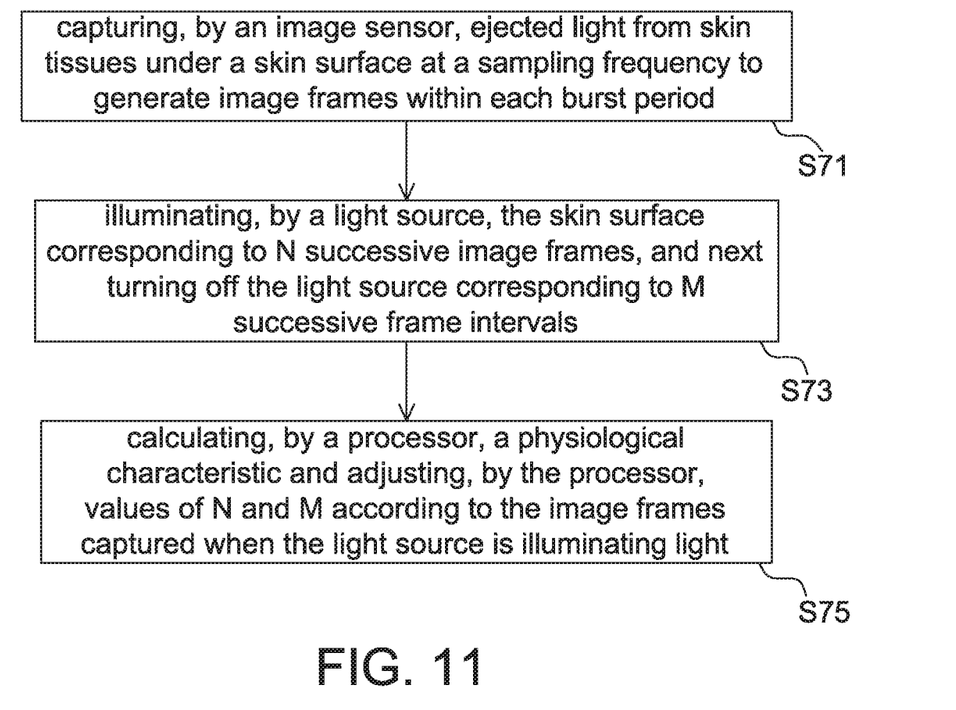
FIG. 11 is a flow chart of an operating method of a physiological detection device according to one embodiment of the present disclosure.

Please referring to FIG. 11, it is a flow chart of an operating method of a physiological detection device according to one embodiment of the present disclosure, which is applicable to the physiological detection device 600 of FIG. 6. The operating method includes the steps of: capturing, by an image sensor, ejected light from skin tissues under a skin surface at a sampling frequency to successively generate image frames (Step S71); illuminating, by a light source, the skin surface corresponding to N successive image frames, and next turning off the light source corresponding to M successive frame intervals (Step S73); and calculating, by a processor, a physiological characteristic and adjusting, by the processor, values of N and M according to the image frames captured when the light source is illuminating light (Step S75).

Steps S71-S73: The image sensor 62 is arranged on a skin surface S as shown in FIGS. 6, 8A and 8B, and receives ejected light from skin tissues under the skin surface S at a fixed sampling frequency as shown in FIG. 9 to output a preoperative image Ip and valid image frames $I_1$ corresponding to the turning on of the light source 61. In the embodiment of FIGS. 9, N=5 and M=495, but the present disclosure is not limited thereto.

Step S75: The processor 63 calculates an image quality or an operating state parameter according to the image frames captured when the light source 61 is illuminating light (e.g., valid, image frames $I_1$). For example, the processor 63 adjusts values of N and M according to a comparison between the image quality and at least one quality threshold, wherein the image quality has been illustrated above and thus details thereof are not repeated herein. For example, the processor 63 increases N when the operating state parameter indicates a sports state, and decreases N when the operating state parameter indicates a rest state, wherein the operating state parameter has been illustrated above and thus details thereof are not repeated herein.

Figure 12:
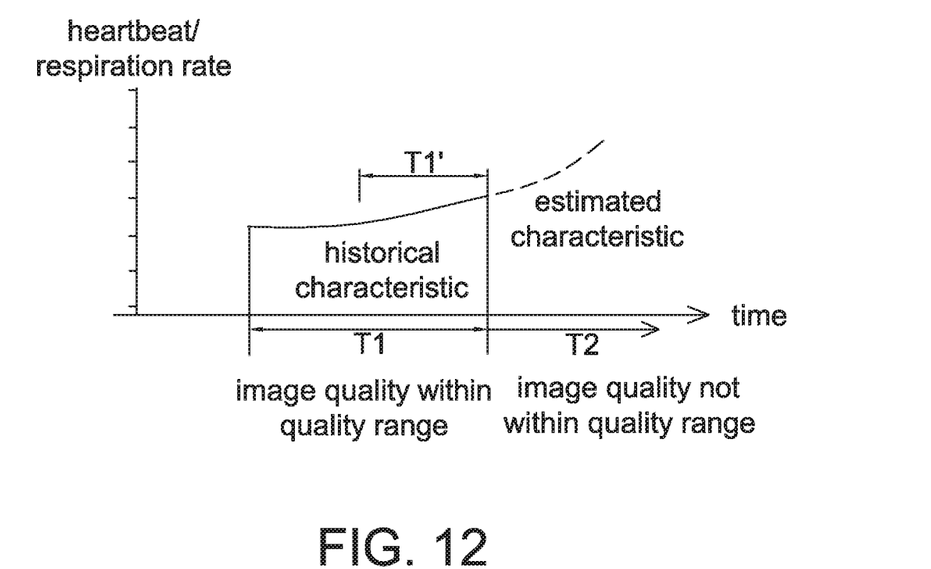
FIG. 12 is a schematic diagram of a physiological variation according to one embodiment of the present disclosure.

In the present disclosure, when the image quality calculated by the processor 63 after the value of N is increased is still not within a quality range, the processor 63 is further configured to generate estimated physiological characteristics according to historical physiological characteristics. For example referring to FIG. 12, when a user changes his/her state from the rest state to the sports state (identified according to the acceleration signal Sg or the waveform of PPG signal as mentioned above), the processor 63 increase the value of N (e.g., adjusting from N=5 to N=9 or 17, but not limited thereto). When the value of N is increased and if the image quality calculated according to the increased N valid image frames I₁ is still not within a predetermined quality range, it means that the image quality cannot be effectively increased by increasing N, wherein the predetermined quality range is previously set as being able to correctly calculate the physiological characteristic. In this case, the processor 63 uses a variation trend of the physiological characteristic calculated according to the previous valid image frames I₁ having the image quality within the predetermined quality range (e.g., interval T1) to predict the physiological characteristic for the interval (e.g., T2) during which the image quality of the captured valid image frames I₁ is not within the predetermined quality threshold to be served as estimated physiological characteristics. That is, the estimated physiological characteristic is not calculated according to current valid image frames I₁, but predicted according to the variation (e.g., curve slope or fitting equation during the interval T1') of the physiological characteristic calculated according to the previously captured valid image frames I₁ having the image quality within the predetermined quality range.

In some embodiments, when the image quality calculated by the processor 63 according to the increased N valid image frames I₁ is still not within a predetermined quality range, the physiological characteristic is not generated. For example, the processor 63 controls the display device 69 to show characters or a graph about "FAIL".

In the present disclosure, the above image quality and operating state parameter and their corresponding N, M and thresholds are previously stored in a memory 631 before shipment, wherein the memory 631 may be inside or outside of the processor 63 without particular limitations as long as the processor 63 is able to access the memory 631. The memory 631 is preferably a nonvolatile memory. It is appreciated that when the value of N is changed, the value of M is changed correspondingly. In some embodiments, the stored N, M and thresholds may be updated by the user during operation.

In some embodiments, the above operating state parameter is served as the image quality since when a user enters a sports state, the image quality is generally reduced correspondingly. In some embodiments, the above image quality is used to indicate a user's state, For example, when the image quality is smaller than a quality threshold, the processor 63 identifies that the user is in a sports state; on the contrary, when the image quality is larger than the quality threshold, the processor 63 identifies that the user is in a rest state. Then, it is able to adjust the values of N and M according to the embodiments mentioned above based on the image quality or operating state parameter.

As mentioned above, as functions of the portable electronic device and the wearable electronic device are gradually increased, it is necessary to reduce the total power consumption thereof The present disclosure further provides a physiological detection device (FIG. 6) and an operating method thereof (FIG. 11) that are applicable to the portable electronic device and the wearable electronic device and employ so-called burst mode in both the image sensor and the light source to effectively reduce the total power consumption in operation.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A physiological detection device, comprising:
   an image sensor comprising a sensor array which has a pixel number, and configured to receive, at a sampling frequency, ejected light from skin tissues under a skin surface to generate image frames;
   a light source configured to illuminate the skin surface using a burst mode, wherein in the burst mode, the light source is configured to turn on corresponding to N successive image frames and next turn off corresponding to M successive frame intervals;
   a processor configured to
   control the light source and the image sensor, and
   calculate a physiological characteristic according to the image frames captured when the light source is turned on; and
   a transmission interface configured to output the physiological characteristic at a report rate,
   wherein the processor is further configured to adjust values of N and M according to an image quality of the image frames, wherein (N+M) is a quotient calculated by dividing the sampling frequency by a product of the report rate and the pixel number.

2. The physiological detection device as claimed in claim 1, wherein the processor is configured to
   calculate a first heartbeat at a time domain and a second heartbeat at a frequency domain according to the image frames captured when the light source is turned on, and
   use a difference value between the first heartbeat and the second heartbeat as the image quality.

3. The physiological detection device as claimed in claim 1, wherein the processor is configured to
   obtain a main frequency spectrum energy of a main frequency at a frequency domain according to the image frames captured when the light source is turned on,
   multiply the main frequency spectrum energy by a predetermined ratio smaller than 1 to obtain an energy threshold, and
   use a number of frequencies whose spectrum energy is larger than the energy threshold as the image quality.

4. The physiological detection device as claimed in claim 1, wherein processor is configured to
   obtain a main frequency spectrum energy of a main frequency at frequency domain according to the image frames captured when the light source is turned on,
   multiply the main frequency spectrum energy by a predetermined ratio smaller than 1 to obtain an energy threshold, and
   use a sum of spectrum energy of frequencies whose spectrum energy is larger than the energy threshold as the image quality.

5. The physiological detection device as claimed in claim 1, wherein when the image quality calculated by the processor after the value of N is increased is not within a quality range, the processor is further configured to generate estimated physiological characteristics according to historical physiological characteristics.

6. The physiological detection device as claimed in claim 1, wherein N is larger than or equal to 5.

7. A physiological detection device, comprising:
an image sensor comprising a sensor array which has a pixel number and configured to receive, at a sampling frequency, ejected light from skin tissues under a skin surface to generate image frames;
a light source configured to illuminate the skin surface using a burst mode, wherein in the burst mode, the light source is configured to turn on corresponding to N successive image frames and next turn off corresponding to M successive frame intervals;
a processor configured to
control the light source and the image sensor, and
calculate a physiological characteristic and an operating state parameter according to the image frames captured when the light source is turned on; and
a transmission interface configured to output the physiological characteristic at a report rate,
wherein the processor is further configured to adjust values of N and M according to the operating state parameter, wherein (N+M) is a quotient calculated by dividing the sampling frequency by a product of the report rate and the pixel number.

8. The physiological detection device as claimed in claim 7, wherein the processor is further configured to
generate a photoplethysmography (PPG) signal according to the image frames captured when the light source is turned on, and
use a waveform variation of the PPG signal as the operating state parameter.

9. The physiological detection device as claimed in claim 7, further comprising a G sensor configured to output an acceleration signal, and the processor is further configured to use the acceleration signal as the operating state parameter.

10. The physiological detection device as claimed in claim 7, wherein
when the operating state parameter indicates a sports state, the processor is configured to use a larger N among pre-stored N values, and
when the operating state parameter indicates a rest state, the processor is configured to use a smaller N among the pre-stored N values.

11. The physiological detection device as claimed in claim 10, wherein
the processor is further configured to calculate an image quality according to the image frames captured when the light source is turned on, and
when the image quality calculated by the processor after the value of N is increased is not within a quality range, the processor is further configured to generate estimated physiological characteristics according to historical physiological characteristics.

12. The physiological detection device as claimed in claim 7, wherein N is larger than or equal to 5.

13. An operating method of a physiological detection device, the physiological detection device comprising a light source, an image sensor comprising a sensor array which has a pixel number, and a processor, the operating method comprising:
capturing, by the image sensor, ejected light from skin tissues under a skin surface at a sampling frequency to generate image frames;
illuminating, by the light source, the skin surface corresponding to N successive image frames, and next turning off the light source corresponding to M successive frame intervals;
calculating, by the processor, a physiological characteristic according to the image frames captured when the light source is illuminating light;
outputting the physiological characteristic at a report rate; and
adjusting values of N and M according to an image quality of the image frames, wherein (N+M) is a quotient calculated by dividing the sampling frequency by a product of the report rate and the pixel number.

14. The operating method as claimed in claim 13, further comprising:
calculating, by the processor, the image quality according to the image frames captured when the light source is illuminating light, and
adjusting the values of N and M according to a comparison between the image quality and at least one quality threshold.

15. The operating method as claimed in claim 13, further comprising:
calculating, by the processor, an operating state parameter according to the image frames captured when the light source is illuminating light;
increasing N when the operating state parameter indicates a sports state; and
decreasing N when the operating state parameter indicates a rest state.

16. The operating method as claimed in claim 13, further comprising:
reporting the physiological characteristic every a report period, wherein the N successive image frames correspond to an initial interval of the report period and N is larger than or equal to 5.

* * * * *